United States Patent [19]
Knudsen

[11] Patent Number: 6,158,584
[45] Date of Patent: Dec. 12, 2000

[54] TRACH TIE CARE ASSEMBLY

[76] Inventor: Sharon K. Knudsen, 170 Greenwood Dr., Galloway, Ohio 43119

[21] Appl. No.: 09/375,761

[22] Filed: Aug. 18, 1999

[51] Int. Cl.[7] .................................................. B65D 83/10
[52] U.S. Cl. ........................................... 206/363; 206/438
[58] Field of Search ..................................... 206/363, 364, 206/438, 338, 570; 128/DIG. 15, 207.17

[56] References Cited

U.S. PATENT DOCUMENTS 4,331,144  5/1982  Wapner ........................ 128/207.11

Primary Examiner—Paul T. Sewell
Assistant Examiner—Shian Luong
Attorney, Agent, or Firm—Thomas S. Baker, Jr.

[57] ABSTRACT

An assembly for stowing and laundering trach ties is provided with a semi-rigid trach tie carrier and with a compliant laundry bag element that is attached, inverted and "inside-out", to the trach tie carrier and that envelops the trach tie carrier when manipulated to an "outside-out" condition.

5 Claims, 5 Drawing Sheets

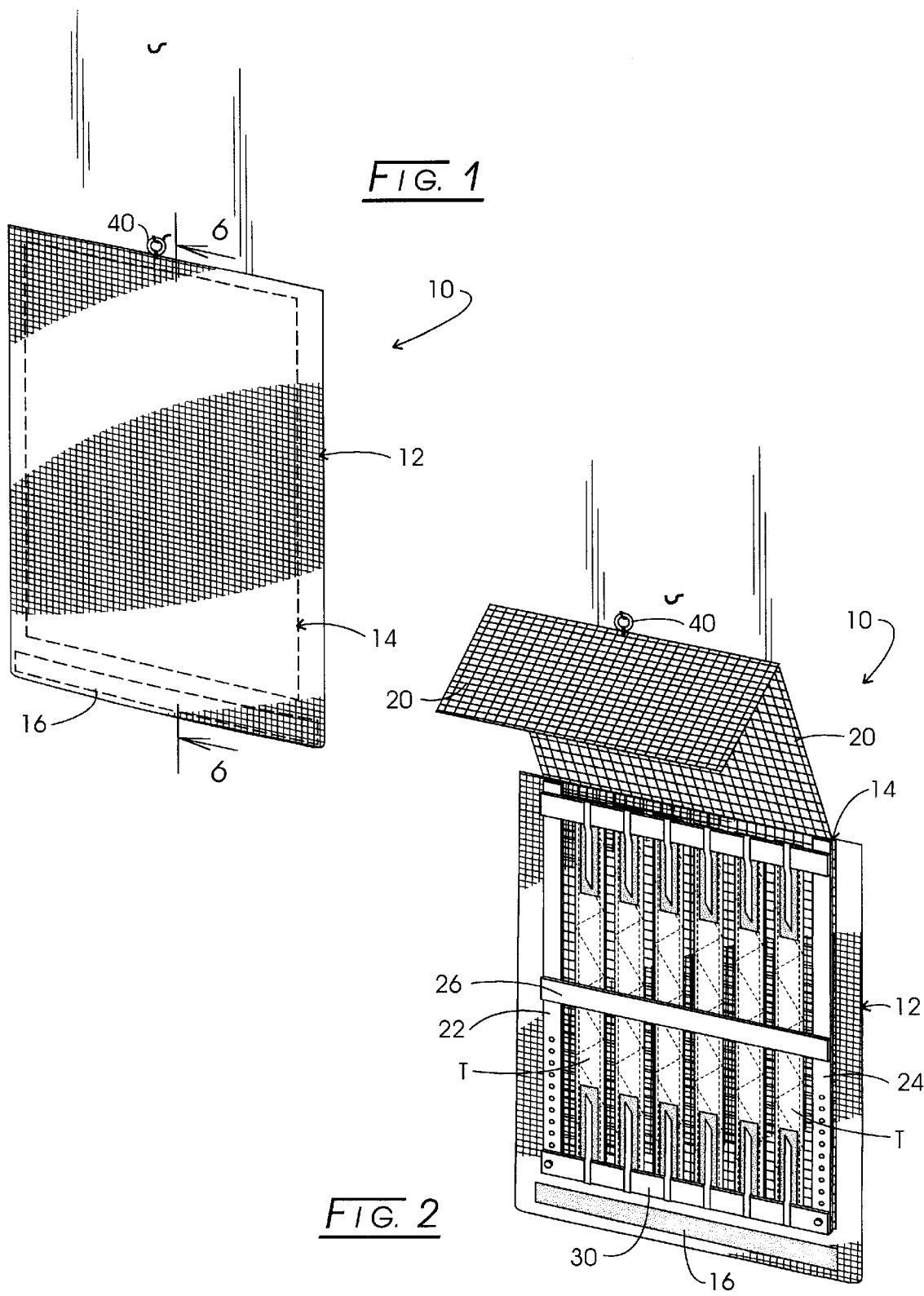

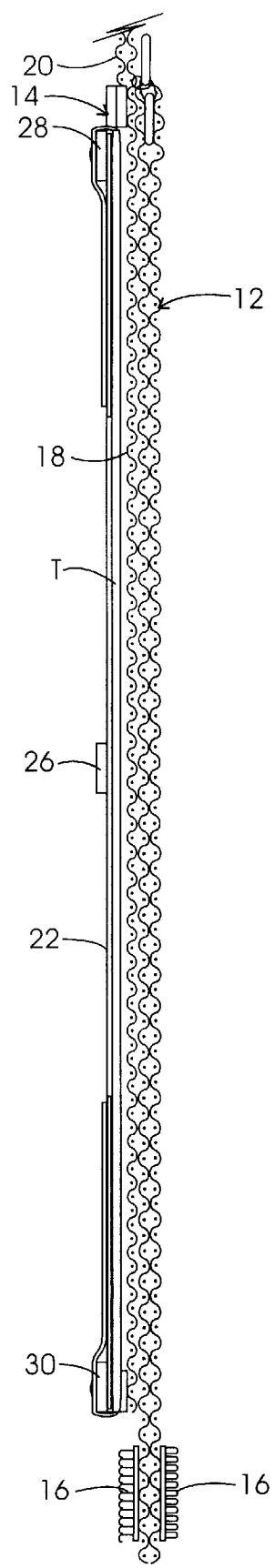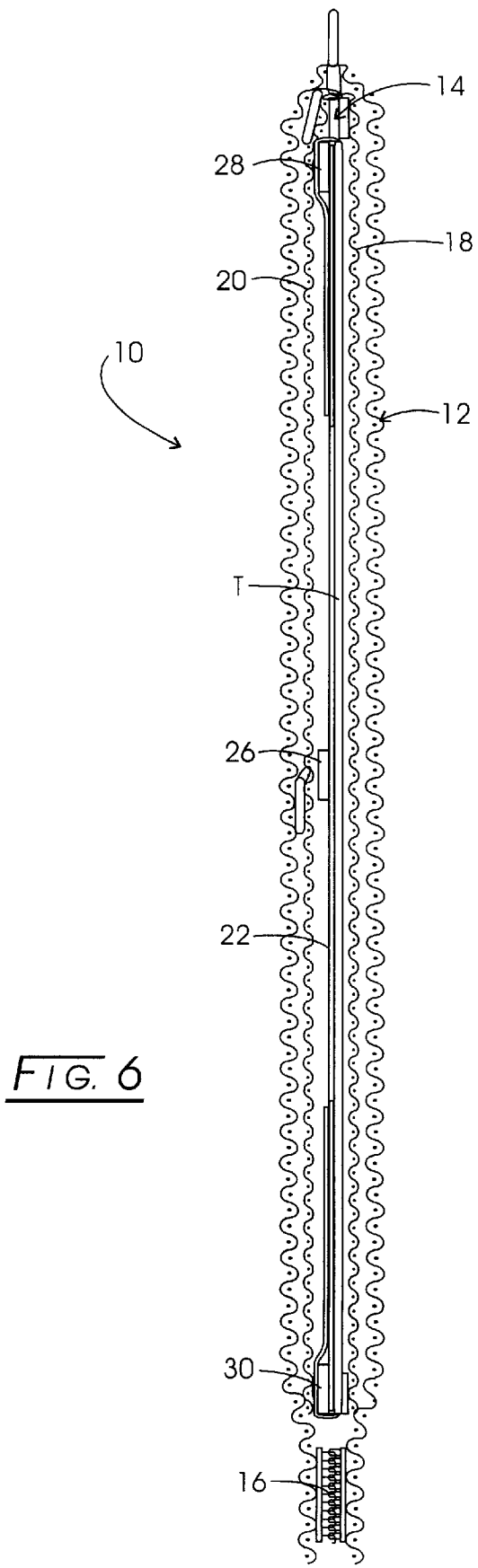
FIG. 5
FIG. 6

TRACH TIE CARE ASSEMBLY

BACKGROUND OF THE INVENTION

Heretofore it has been common practice to have tracheostomy patients utilize disposable trach ties of the general configuration disclosed in U.S. Pat. No. 4,331,144 issued to Wapner for retaining their endotracheal tube medical appliances in proper position, with intermittent disposal of soiled ties for replacement with new disposable ties. It has been recognized that substantial trach tie cost savings can be realized, by providing reuseable cloth trach ties, suitable for repeated laundering and reusing such ties, but no satisfactory gear or kits have been available for conveniently accomplishing that objective.

Accordingly, it is an object of the present invention to provide a trach tie care assembly that may be conveniently utilized for the stowing of clean trach ties, for the stowing of soiled trach ties, and for the laundering of soiled trach ties. Another objective of the invention is to provide such a care assembly that may be wall-hung for convenience.

Other objects and advantages of the present invention will become apparent during consideration of the descriptions and claims which follow.

SUMMARY OF THE INVENTION

The trach tie unit of the present invention is basically an assembly comprised of a semi-rigid tie carrier element and a flexible plastic mesh or woven fiber laundry bag element attached to the top of the tie carrier inverted and "inside-out". Normally the laundry bag element hangs over the front of the carrier element to overlie contained clean and soiled trach ties such that they are covered and not subject to accidental contact. However, the laundry bag can also be flipped over the tie carrier element for easier access to contained trach ties. The tie carrier element is provided with a mesh base, with pair of side rails placed upon and attached to the mesh base, with a horizontal center rail placed upon and attached to the side rails, with vertically-adjustable, horizontal, top and bottom cross rails also placed upon and attached to the side rails, and with an articulated mesh cover secured to the mesh base and positioned over the assembly horizontal cross rails.

Individual trach ties, whether cleaned or soiled, are each fastened at their respective ends to the tie carrier after looping around the element top and bottom horizontal cross rails and also following after being passed under the tie carrier element center cross rail. When the tie carrier element is filled with soiled trach ties that are to be laundered for reuse, the carrier mesh cover is positioned over the secured trach ties and the unit laundry bag element is progressively turned from "inside-out" to "inside-in" from its zone of attachment to below the tie carrier bottom cross rail and mesh base thereby enveloping the tie carrier element and contained soiled trach ties with the mesh laundry bag element.

The assembled combination of elements and reusable trach ties are subsequently conventionally laundered, air-dried, and readied for reuse by turning the laundry bag element envelope "outside-in" from the bottom of the assembly progressively toward the zone of element attachment at the top of the trach tie carrier element.

Extensive use is made of non-absorbent materials such as conventional molded nylon resins, molded polypropylene resins, and molded high-density polyethylene resins, and the like in the manufacture of the various component parts of the invention trach tie unit.

BRIEF DESCRIPTION OF THE DRAWINGS

FIG. 1 is a perspective view of the trach tie care assembly of the present invention illustrated in its ready-for-laundering condition;

FIG. 2 is a perspective view of the tie carrier portion of the trach tie care assembly of FIG. 1 in a partially-opened condition;

FIG. 5 is a section view taken at line 5—5 of FIG. 3;

FIG. 6 is a section view taken at line 6—6 of FIG. 1;

DETAILED DESCRIPTION

FIG. 1 illustrates the trach tie case assembly 10 of the present invention in its assembled and ready-to-launder condition with its exterior laundry bag element 12 enveloping the assembly trach tie carrier element 14 (see FIG. 6 and FIGS. 2 through 4). A conventional "Velcro"™ fastener 16 is provided at the laundry bag element open end interior to obtain complete closure for the interiorly-contained trach tie carrier element.

Figure 3:
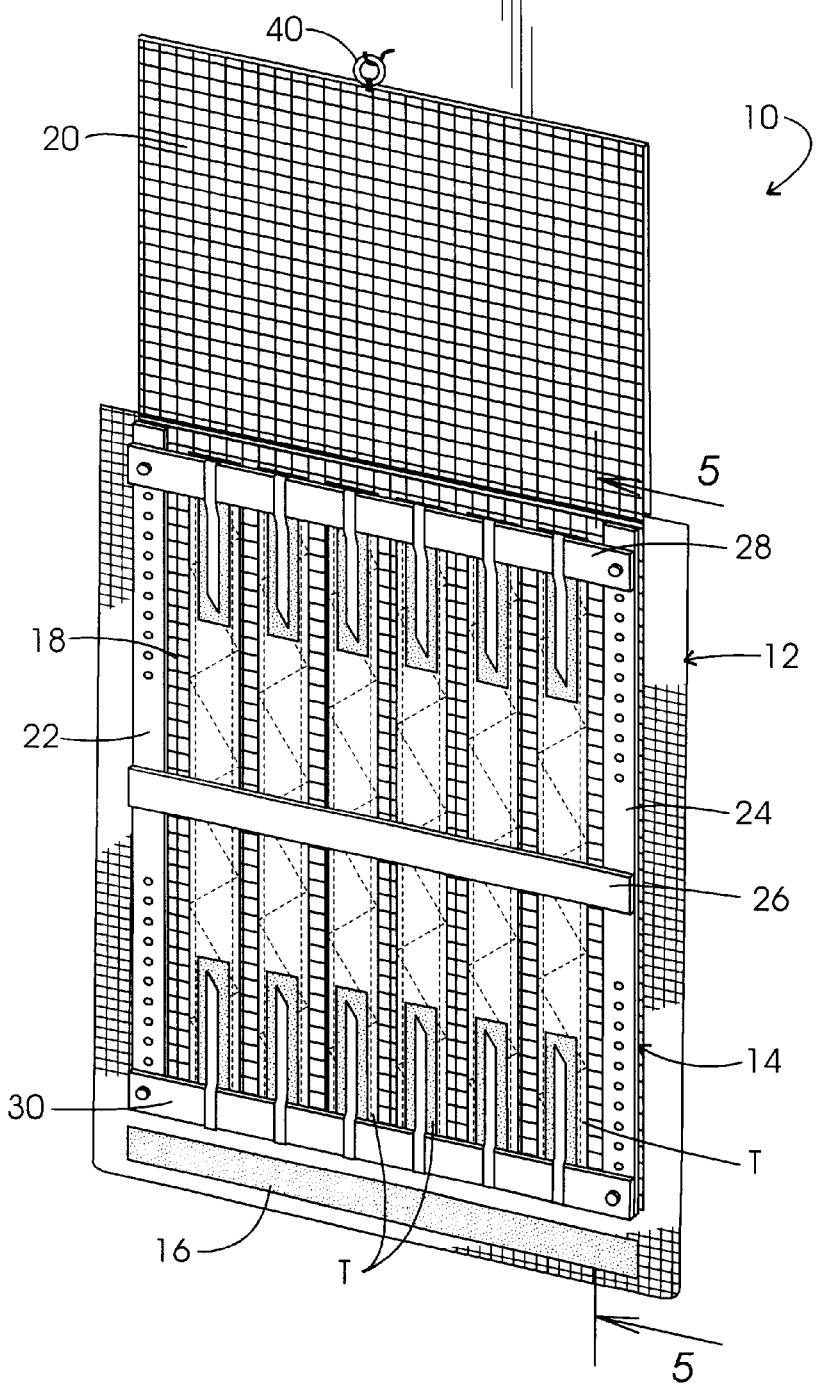
FIG. 3 is a perspective view of the tie carrier portion of the assembly of FIG. 1 in a fully-opened condition.
Figure 4:
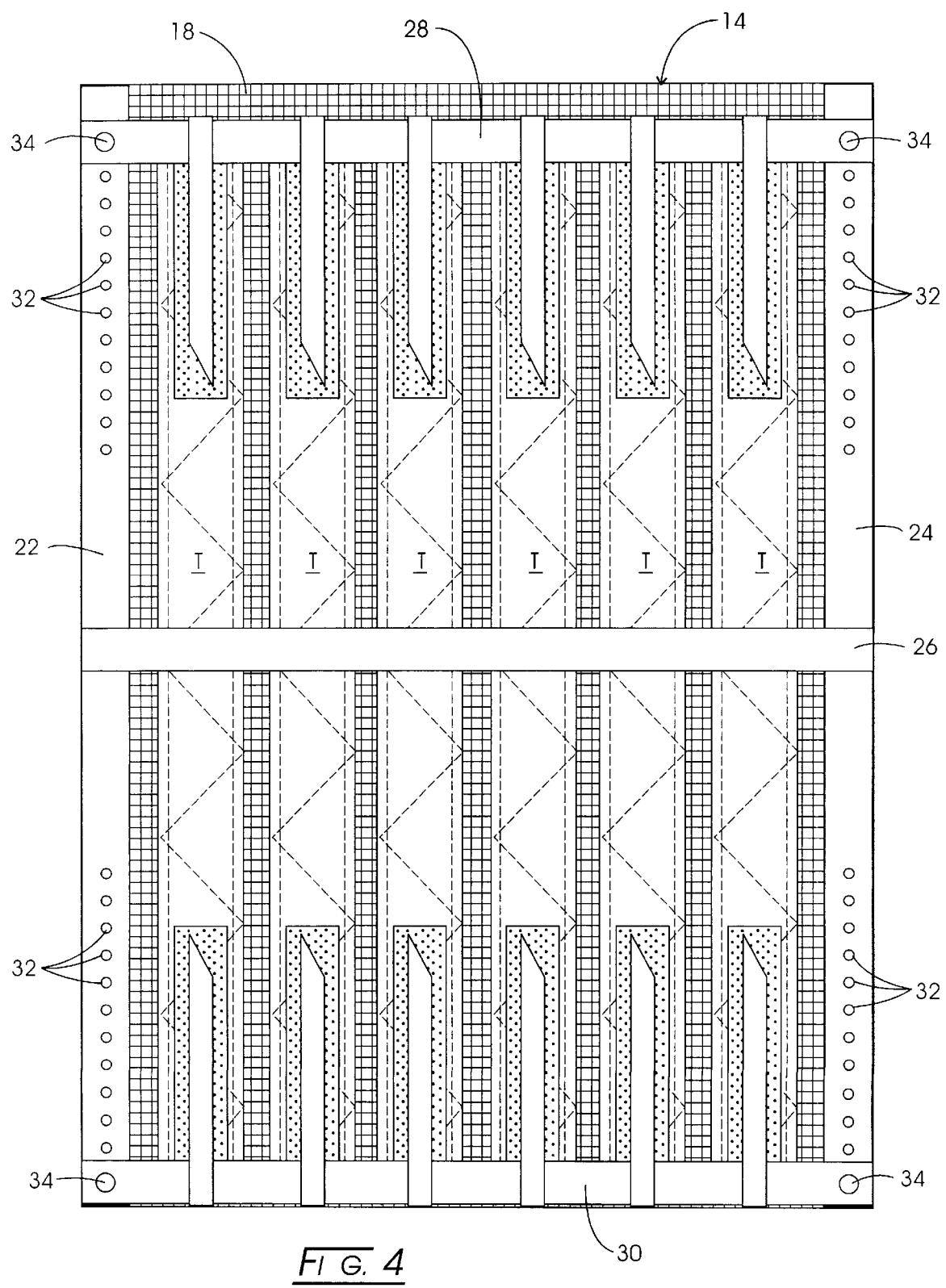
FIG. 4 is an elevation view of the tie carrier portion of FIGS. 2 and 3 at a larger scale.

As shown in FIGS. 2, 3, and 4, trach tie carrier element 14 is basically comprised of a semi-rigid, planar mesh back element 18, an articulated and hinged planar mesh cover element 20 hingedly joined to the top of mesh back element 18 and also hinged at its center, comparatively rigid side-rail elements 22 and 24 joined to and carried by mesh back element 18, a comparatively rigid center cross-rail element 26 positioned upon, attached to, and carried by side rail elements 22 and 24, and comparatively rigid top and bottom cross-rail elements 28 and 30 also positioned upon, carried by, but adjustably attached to side-rail elements 22 and 24. Snap fastener ball elements 32 are molded integral with side-rail elements 22 and 24, and co-operating snap fastener socket elements 34 are provided integral with the ends of top and bottom cross-rail elements 28 and 30. Trach tie carrier element 14 can be readily modified to accommodate trach ties T of a different length than those previously carried by trach tie unit 10 by adjusting and changing the positions of the snap fastener socket element 34 of top and bottom cross-rail element 28 and 30 relative to particular snap fastener ball elements 32.

When loading soiled trach ties T into unit 10, each trach tie is positioned between center cross-rail element 26 and mesh back element 18, and with its "Velcro"™ fastener ends passed under and looped respectively around top and bottom cross-rail elements 28 and 30 and fastened by attaching them to themselves.

Figure 7:
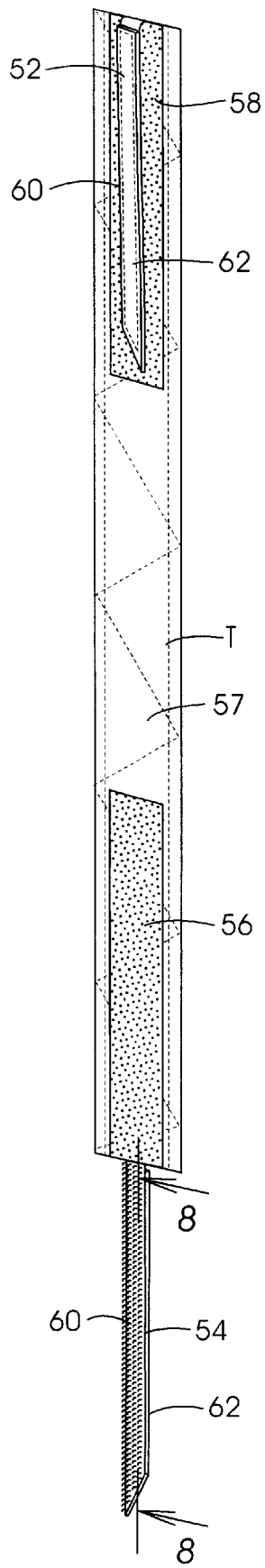
FIG. 7 is a plan view of an improved trach tie assembly that is especially suitable for use with the trach tie care assembly of FIGS. 1 through 6.
Figure 8:
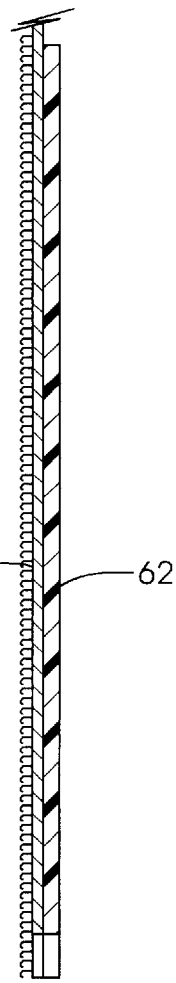
FIG. 8 is a section view taken at line 8—8 of FIG. 7.

In FIGS. 7 and 8 I provide details of a preferred individual trach tie T. Such trach tie basically has a woven fabric neckband 57 and attached tie end portions 52 and 54. Loop-type "Velcro"™ fastener strips 56 and 58 are preferably sewn at their margins to the end margins of neckband 57 and a hook-type "Velcro"™ fastener strip 60 is preferably sewn at its margins to each of integral tie end portions 52 and 54 of neckband 57. In addition, a semi-flexible plastic overlay strip 62 is laminated to each of tie end portions 52 and 54 by sewing to the tie end "Velcro"™ fastener strips.

Such modification provide additional stiffness to the trach tie T tie ends to facilitate their insertion into carrier element 14 behind cross-rail elements 26, 28, and 30.

When trach tie unit 10 is to be readied for subsequent laundering, articulataed cover 20 is fastened to cover carrier element 14 and compliant laundry bag element 12 is caused to envelop loaded trach tie carrier element 14 by inside-out turning from the FIG. 2 inside-out condition with placement in front of trach tie carrier element 14 to the FIG. 1 outside-out condition enveloping carrier element 14. Velcro™ fastener elements 16 are then joined to effect complete closure of laundry bag element 12.

As illustrated in FIGS. 1 through 3, various loop or ring elements 40 are provided in assembly 10 for use in conveniently hanging the trach tie unit on a wall-installed hook.

Various changes may be made in the configuration, relative size, and material of construction of each element of the described invention without departing from the scope, meaning, or intent of the claims which follow

I claim as my invention:

1. A trach tie care assembly for use in stowing clean trach ties and in stowing and laundering soiled trach ties, comprising:

a mesh back element;

a pair of vertical side-rail elements placed upon and attached to said mesh back element in the regions of the sides of said mesh back element;

a top horizontal cross-rail element placed upon and attached to said vertical side-rail elements in the region of a top of said mesh back element;

a bottom horizontal cross-rail element placed upon and attached to said vertical side-rail elements in the region of a bottom of said mesh back element; and a compliant mesh laundry bag element inverted and joined, in an "inside-out" condition, with a closed bottom attached to said mesh back element in the region of the top of said mesh back element, said mesh laundry bag element enveloping said mesh back element and a mesh back element attachments when manipulated to an "outside-out" condition.

2. The trach tie care assembly invention defined by claim 1 wherein said vertical side-rail elements and said top and bottom horizontal cross-rail elements are provided with co-operating snap fastener elements that enable said top and bottom horizontal cross-rail elements to be adjustably positioned at different distances from a center horizontal cross-rail element.

3. The trach tie care assembly invention defined by claim 1 wherein said mesh cover element is hingedly articulated and also hingedly attached to said mesh back element in the region of the top of said mesh back element.

4. The trach tie care assembly invention defined by claim 1 further comprising a center horizontal cross-rail element placed upon and attached to said vertical side-rail element in the region of a center of said mesh back element.

5. The trach tie care assembly defined by claim 1 further comprising a mesh cover element positioned over and hingedly attached to said mesh back element in the region of the top of said mesh back element and enveloped by said mesh laundry bag element when said bag element is in an "outside-out" condition.

\* \* \* \* \*